(12) United States Patent
Bellin et al.

(10) Patent No.: US 9,539,700 B2
(45) Date of Patent: Jan. 10, 2017

(54) HIGH TEMPERATURE HIGH HEATING RATE TREATMENT OF PDC CUTTERS

(71) Applicant: VAREL INTERNATIONAL IND., L.P., Carrollton, TX (US)

(72) Inventors: Federico Bellin, Tomball, TX (US); Vamsee Chintamaneni, Houston, TX (US)

(73) Assignee: VAREL INTERNATIONAL IND., L.P., Carrollton, TX (US)

(*) Notice: Subject to any disclaimer, the term of this patent is extended or adjusted under 35 U.S.C. 154(b) by 0 days.

(21) Appl. No.: 14/978,269

(22) Filed: Dec. 22, 2015

(65) Prior Publication Data
US 2016/0107293 A1 Apr. 21, 2016

Related U.S. Application Data

(63) Continuation of application No. 13/440,868, filed on Apr. 5, 2012, now Pat. No. 9,249,059.

(51) Int. Cl.
*B24D 3/00* (2006.01)
*B24D 3/02* (2006.01)
(Continued)

(52) U.S. Cl.
CPC ............. *B24D 3/06* (2013.01); *B24D 18/00* (2013.01); *C04B 35/52* (2013.01); *C04B 35/5831* (2013.01); *C04B 41/009* (2013.01); *C04B 41/0072* (2013.01); *C04B 41/80* (2013.01); *C21D 1/30* (2013.01); *C21D 1/44* (2013.01); *C21D 11/00* (2013.01); *C22C 1/1094* (2013.01); *C25F 1/00* (2013.01); *G01N 29/14* (2013.01); *B22F 2005/001* (2013.01); *C04B 2235/427* (2013.01); *C04B 2235/6562* (2013.01); *C04B 2235/6567* (2013.01); *C04B 2235/662* (2013.01);
(Continued)

(58) Field of Classification Search
USPC .......................................... 51/307, 293, 309
See application file for complete search history.

(56) References Cited

U.S. PATENT DOCUMENTS

| 6,011,248 A * | 1/2000 | Dennis .................... B22F 3/105 219/700 |
| 2010/0320006 A1* | 12/2010 | Fan ....................... B24D 99/005 175/428 |

(Continued)

*Primary Examiner* — James McDonough

(57) ABSTRACT

A post manufacture method and apparatus for reducing residual stresses present within a component. The component includes a substrate, a polycrystalline structure coupled thereto, and residual stresses present therein. The method includes obtaining a component from a component category, determining a critical temperature and a critical time period for the component category at which the component becomes structurally impaired, determining a heat treatment temperature and a heat treatment time period based upon the critical temperature and the critical time period, and heating one or more remaining components from the component category to the heat treatment temperature for the heat treatment time period. The apparatus includes a heater defining a heating chamber and a molten bath positioned within the heating chamber. The components are placed within the pre-heated molten bath and isolated from oxygen during heating to the heat treatment temperature for the heat treatment time period.

7 Claims, 8 Drawing Sheets

(51) Int. Cl.
*B24D 11/00* (2006.01)
*B24D 18/00* (2006.01)
*C09K 3/14* (2006.01)
*B24D 3/06* (2006.01)
*C04B 35/52* (2006.01)
*C04B 35/5831* (2006.01)
*C04B 41/00* (2006.01)
*C21D 1/30* (2006.01)
*C21D 1/44* (2006.01)
*C21D 11/00* (2006.01)
*C04B 41/80* (2006.01)
*C22C 1/10* (2006.01)
*G01N 29/14* (2006.01)
*C25F 1/00* (2006.01)
*C22C 26/00* (2006.01)
*B22F 5/00* (2006.01)

(52) U.S. Cl.
CPC ...... *C04B 2235/664* (2013.01); *C04B 2235/96* (2013.01); *C22C 26/00* (2013.01); *G01N 2291/0232* (2013.01)

(56) References Cited

U.S. PATENT DOCUMENTS

2011/0132667 A1\* 6/2011 Smallman ................ B01J 3/062
  175/428
2011/0239765 A1\* 10/2011 Bellin ...................... G01N 3/44
  73/587

\* cited by examiner

HIGH TEMPERATURE HIGH HEATING RATE TREATMENT OF PDC CUTTERS

RELATED APPLICATIONS

The present application is related to U.S. patent application Ser. No. 12/754,784, entitled "Acoustic Emission Toughness Testing For PDC, PCBN, Or Other Hard Or Superhard Material Inserts" and filed on Apr. 6, 2010, which is incorporated by reference herein.

TECHNICAL FIELD

The present invention is directed generally to cutters having a polycrystalline structure; and more particularly, to a post manufacture method and apparatus for reducing residual stresses present within the cutters and to a cutter having reduced residual stresses upon undergoing treatment after its manufacture.

BACKGROUND

Polycrystalline diamond compacts ("PDC") have been used in industrial applications, including rock drilling applications and metal machining applications. Such compacts have demonstrated advantages over some other types of cutting elements, such as better wear resistance and impact resistance. The PDC can be formed by sintering individual diamond particles together under the high pressure and high temperature ("HPHT") conditions referred to as the "diamond stable region," which is typically above forty kilobars and between 1,200 degrees Celsius and 2,000 degrees Celsius, in the presence of a catalyst/solvent which promotes diamond-diamond bonding. Some examples of catalyst/solvents for sintered diamond compacts are cobalt, nickel, iron, and other Group VIII metals. PDCs usually have a diamond content greater than seventy percent by volume, with about eighty percent to about ninety-eight percent being typical. An unbacked PDC can be mechanically bonded to a tool (not shown), according to one example. Alternatively, the PDC is bonded to a substrate, thereby forming a PDC cutter, which is typically insertable within, or mounted to, a downhole tool (not shown), such as a drill bit or a reamer.

FIG. 1 shows a side view of a PDC cutter 100 having a polycrystalline diamond ("PCD") cutting table 110, or compact, in accordance with the prior art. Although a PCD cutting table 110 is described in the exemplary embodiment, other types of cutting tables, including polycrystalline boron nitride ("PCBN") compacts, are used in alternative types of cutters. Referring to FIG. 1, the PDC cutter 100 typically includes the PCD cutting table 110 and a substrate 150 that is coupled to the PCD cutting table 110. The PCD cutting table 110 is about one hundred thousandths of an inch (2.5 millimeters) thick; however, the thickness is variable depending upon the application in which the PCD cutting table 110 is to be used.

The substrate 150 includes a top surface 152, a bottom surface 154, and a substrate outer wall 156 that extends from the circumference of the top surface 152 to the circumference of the bottom surface 154. The PCD cutting table 110 includes a cutting surface 112, an opposing surface 114, and a PCD cutting table outer wall 116 that extends from the circumference of the cutting surface 112 to the circumference of the opposing surface 114. The opposing surface 114 of the PCD cutting table 110 is coupled to the top surface 152 of the substrate 150. Typically, the PCD cutting table 110 is coupled to the substrate 150 using a high pressure and high temperature ("HPHT") press. However, other methods known to people having ordinary skill in the art can be used to couple the PCD cutting table 110 to the substrate 150. In one embodiment, upon coupling the PCD cutting table 110 to the substrate 150, the cutting surface 112 of the PCD cutting table 110 is substantially parallel to the substrate's bottom surface 154. Additionally, the PDC cutter 100 has been illustrated as having a right circular cylindrical shape; however, the PDC cutter 100 is shaped into other geometric or non-geometric shapes in other exemplary embodiments. In certain exemplary embodiments, the opposing surface 114 and the top surface 152 are substantially planar; however, the opposing surface 114 and the top surface 152 is non-planar in other exemplary embodiments. Additionally, according to some exemplary embodiments, a bevel (not shown) is formed around at least a portion of the circumference of the cutting surface 112.

According to one example, the PDC cutter 100 is formed by independently forming the PCD cutting table 110 and the substrate 150, and thereafter bonding the PCD cutting table 110 to the substrate 150. Alternatively, the substrate 150 is initially formed and the PCD cutting table 110 is subsequently formed on the top surface 152 of the substrate 150 by placing polycrystalline diamond powder onto the top surface 152 and subjecting the polycrystalline diamond powder and the substrate 150 to a high temperature and high pressure process. Alternatively, the substrate 150 and the PCD cutting table 110 are formed and bonded together at about the same time. Although a few methods of forming the PDC cutter 100 have been briefly mentioned, other methods known to people having ordinary skill in the art can be used.

According to one example for forming the PDC cutter 100, the PCD cutting table 110 is formed and bonded to the substrate 150 by subjecting a layer of diamond powder and a mixture of tungsten carbide and cobalt powders to HPHT conditions. The cobalt is typically mixed with tungsten carbide and positioned where the substrate 150 is to be formed. The diamond powder is placed on top of the cobalt and tungsten carbide mixture and positioned where the PCD cutting table 110 is to be formed. The entire powder mixture is then subjected to HPHT conditions so that the cobalt melts and facilitates the cementing, or binding, of the tungsten carbide to form the substrate 150. The melted cobalt also diffuses, or infiltrates, into the diamond powder and acts as a catalyst for synthesizing diamond bonds and forming the PCD cutting table 110. Thus, the cobalt acts as both a binder for cementing the tungsten carbide and as a catalyst/solvent for sintering the diamond powder to form diamond-diamond bonds. The cobalt also facilitates in forming strong bonds between the PCD cutting table 110 and the cemented tungsten carbide substrate 150.

Cobalt has been a preferred constituent of the PDC manufacturing process. Traditional PDC manufacturing processes use cobalt as the binder material for forming the substrate 150 and also as the catalyst material for diamond synthesis because of the large body of knowledge related to using cobalt in these processes. The synergy between the large bodies of knowledge and the needs of the process have led to using cobalt as both the binder material and the catalyst material. However, as is known in the art, alternative metals, such as iron, nickel, chromium, manganese, and tantalum, and other suitable materials, can be used as a catalyst for diamond synthesis. When using these alternative materials as a catalyst for diamond synthesis to form the PCD cutting table 110, cobalt, or some other material such as nickel chrome or iron, is typically used as the binder material for cementing the tungsten carbide to form the substrate 150. Although some materials, such as tungsten carbide and cobalt, have been provided as examples, other materials known to people having ordinary skill in the art can be used to form the substrate 150, the PCD cutting table 110, and form bonds between the substrate 150 and the PCD cutting table 110.

FIG. 2 is a schematic microstructural view of the PCD cutting table 110 of FIG. 1 in accordance with the prior art. Referring to FIGS. 1 and 2, the PCD cutting table 110 has diamond particles 210 bonded to other diamond particles 210, one or more interstitial spaces 212 formed between the diamond particles 210, and cobalt 214 deposited within the interstitial spaces 212. During the sintering process, the interstitial spaces 212, or voids, are formed between the carbon-carbon bonds and are located between the diamond particles 210. The diffusion of cobalt 214 into the diamond powder results in cobalt 214 being deposited within these interstitial spaces 212 that are formed within the PCD cutting table 110 during the sintering process.

Once the PCD cutting table 110 is formed and placed into operation, the PCD cutting table 110 is known to wear quickly when the temperature reaches a critical temperature. This critical temperature is about 750 degrees Celsius and is reached when the PCD cutting table 110 is cutting rock formations or other known materials. The high rate of wear is believed to be caused by the differences in the thermal expansion rate between the diamond particles 210 and the cobalt 214 and also by the chemical reaction, or graphitization, that occurs between cobalt 214 and the diamond particles 210. The coefficient of thermal expansion for the diamond particles 210 is about $1.0 \times 10^{-6}$ millimeters$^{-1} \times$ Kelvin$^{-1}$ ("mm$^{-1}$K$^{-1}$"), while the coefficient of thermal expansion for the cobalt 214 is about $13.0 \times 10^{-6}$ mm$^{-1}$K$^{-1}$. Thus, the cobalt 214 expands much faster than the diamond particles 210 at temperatures above this critical temperature, thereby making the bonds between the diamond particles 210 unstable. The PCD cutting table 110 generally becomes thermally degraded at temperatures above about 750 degrees Celsius and its cutting efficiency deteriorates significantly.

Regardless of which process is used to manufacture the PDC cutter 100, thermal residual stresses are induced on the PCD cutting table 110, the substrate 150, and at the interface therebetween after cooling of the PDC cutter 100. These thermal residual stresses are generally formed at least because of the different thermal expansion rates between the PCD cutting table 110 and the substrate 150. The thermal residual stresses induced on the PCD cutting table 110 and the substrate 150 can often result in breakage or delamination of the PDC cutter 100 under drilling conditions.

Efforts have been made to reduce the residual stresses formed and improve the cutters' toughness. Typically, the cutters go through thermal cycles in air or inert atmosphere at temperatures ranging from 500° C. up to 700° C. for about several hours. The temperature of the cutter is slowly ramped up to the 500° C. to 700° C. level, held at, that temperature for a period of time (greater than thirty minutes), and then slowly ramped down so as to avoid thermal shock. The higher the temperatures reach during the cycle without damaging the cutter, the better results that are obtained for reducing the residual stresses within the cutter. However, the efficiency of these stress relieving cycles is limited by max temperatures that can be reached without negatively impacting the integrity of the diamond layer, or cutting surface. Reducing these residual stresses provide for a PDC cutter having better structural integrity and can perform a longer time.

BRIEF DESCRIPTION OF THE DRAWINGS

The foregoing and other features and aspects of the invention are best understood with reference to the following description of certain exemplary embodiments, when read in conjunction with the accompanying drawings, wherein.

Figure 1:
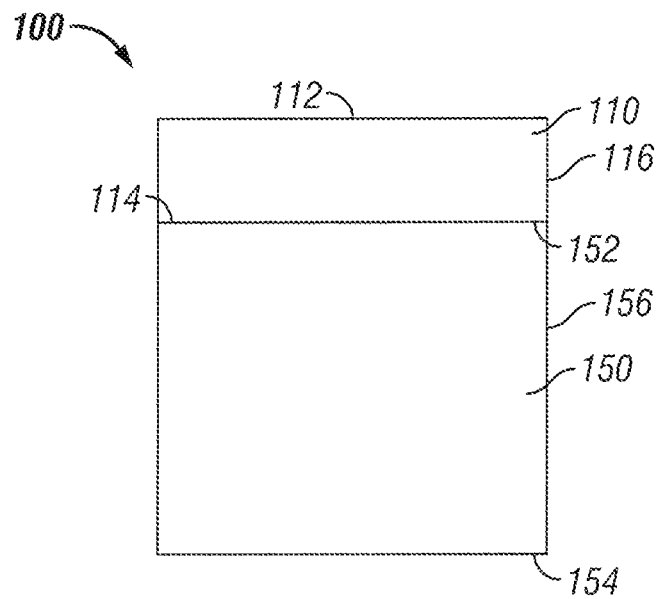
FIG. 1 shows a side view of a PDC cutter having a PCD cutting table in accordance with the prior art.
Figure 2:
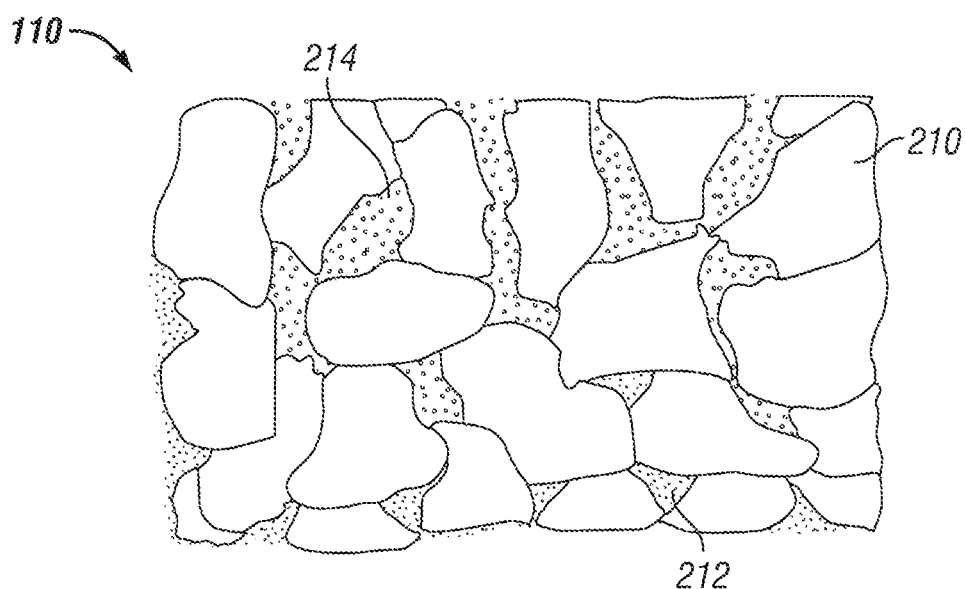
FIG. 2 is a schematic microstructural view of the PCD cutting table of FIG. 1 in accordance with the prior art.

The drawings illustrate only exemplary embodiments of the invention and are therefore not to be considered limiting of its scope, as the invention may admit to other equally effective embodiments.

DETAILED DESCRIPTION

The present invention is directed generally to cutters having a polycrystalline structure; and more particularly, to a post manufacture method and apparatus for reducing residual stresses present within the cutters and to a cutter having reduced residual stresses upon undergoing treatment after its manufacture. Although the description of exemplary embodiments is provided below in conjunction with a polycrystalline diamond compact ("PDC") cutter, alternate embodiments of the invention may be applicable to other types of cutters or components having a polycrystalline structure including, but not limited to, polycrystalline boron nitride ("PCBN") cutters or PCBN compacts. As previously mentioned, the compact is mountable to a substrate to form a cutter or is mountable directly to a tool for performing cutting processes. The invention is better understood by reading the following description of non-limiting, exemplary embodiments with reference to the attached drawings, wherein like parts of each of the figures are identified by like reference characters, and which are briefly described as follows.

Figure 3:
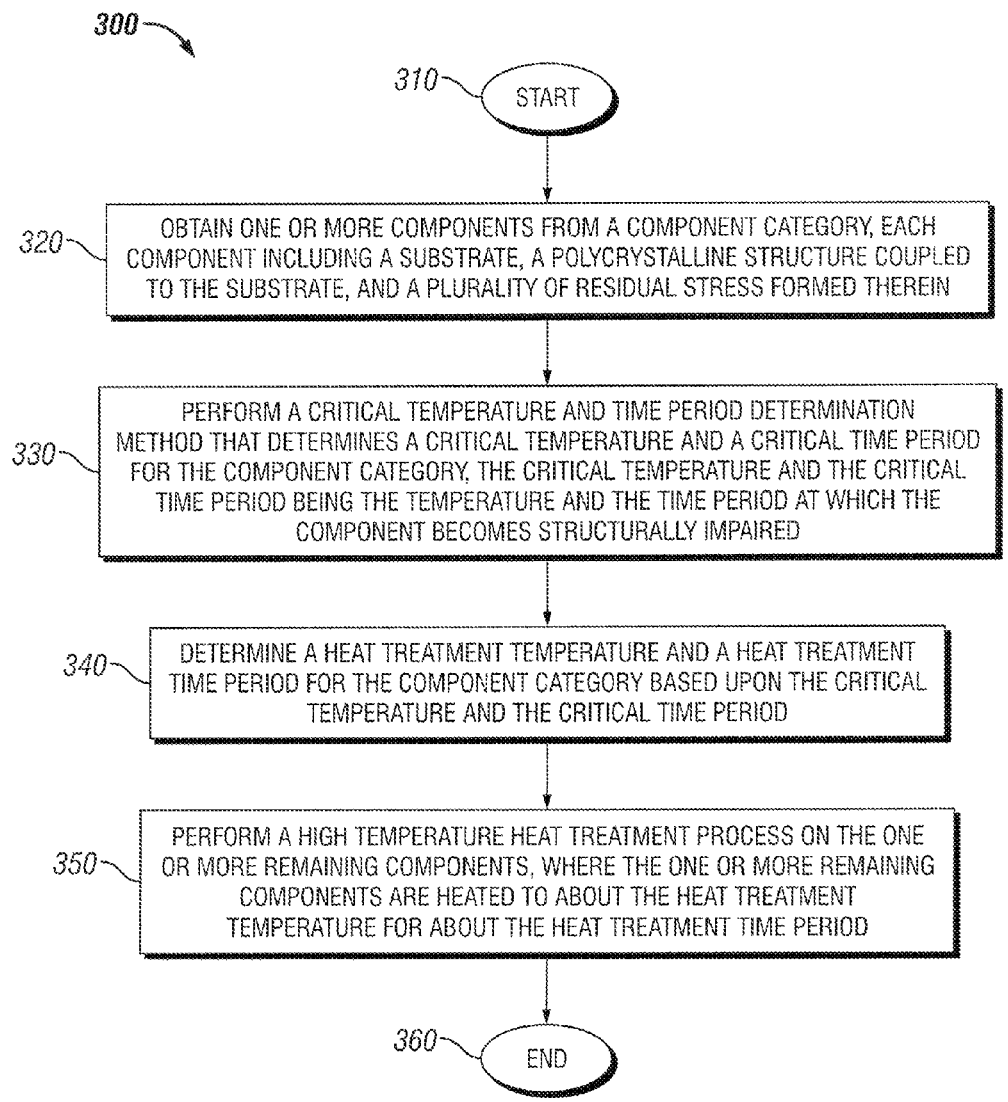
FIG. 3 is a flowchart depicting a residual stress reduction method in accordance with an exemplary embodiment of the present invention.

FIG. 3 is a flowchart depicting a residual stress reduction method 300 in accordance with an exemplary embodiment of the present invention. Although FIG. 3 shows a series of steps depicted in a certain order, the order of one or more steps can be rearranged, combined into fewer steps, and/or separated into more steps than that shown in other exemplary embodiments. Referring to FIG. 3, the residual stress reduction method 300 begins at step 310. Upon starting at step 310, the residual stress reduction method 300 proceeds to step 320.

At step 320, one or more components are obtained from a component category. Each component includes a substrate, a polycrystalline structure coupled to the substrate, and a plurality of residual stresses formed therein. One example of the component is the PDC cutter 100 (FIG. 1) described above, however, other components can be used in lieu of the PDC cutter 100 (FIG. 1). In some exemplary embodiments, the components are categorized into a component category pursuant to the grain size that the polycrystalline structure was fabricated. However, the components can be categorized into different component categories using some other selective criteria in other exemplary embodiments. Components from the same component category typically exhibit similar characteristics, such that the toughness and integrity of the polycrystalline structure from one component is predictive of the toughness and structural integrity of other components from the same component category. The substrate mentioned herein is similar to the substrate 150 (FIG. 1) described above and hence is not repeated for the sake of brevity. The polycrystalline structure mentioned herein is similar to the PCD cutting table 110 (FIG. 1) described above and hence is not repeated for the sake of brevity. Although these components have been previously described, other similar type components can be used without departing from the scope and spirit of the exemplary embodiments. The formation of residual stresses also have been described above and is not repeated for the sake of brevity. The residual stresses are formed within the polycrystalline structure, within the substrate, and at the interface between the polycrystalline structure and the substrate. Increase in the amount of residual stresses cause the component to be less tough and become easily damaged at higher temperatures seen during drilling processes. Minimizing the amount of residual stresses benefit these components, e.g. PDC cutters, because they can be operated for longer periods through higher temperatures and hence provide greater profit returns.

In certain alternative exemplary embodiments, one or more transition layers that are known to people having ordinary skill in the art are provided between the polycrystalline structure and the substrate. Further, in certain alternative exemplary embodiments, at least a portion of the polycrystalline structure of the component has at least some of the catalyst materials removed from therein via a leaching process or other catalyst removal process. Some leaching processes are known to people having ordinary skill in the art, but any leaching process or electrochemical removal process can be used on the component to remove the catalyst material from the polycrystalline structure without departing from the scope and spirit of the exemplary embodiment.

The residual stress reduction method 300 proceeds to step 330. At step 330, a critical temperature and time period determination method is performed on the components to determine a critical temperature and a critical time period for the component category. The critical temperature and the critical time period is the temperature and the time period, respectively, at which the component becomes structurally impaired. The critical temperature and time period determination method is described in further detail below with respect to FIGS. 4 and 5.

The residual stress reduction method 300 proceeds to step 340. At step 340, a heat treatment temperature and a heat treatment time period is determined for the component category based upon the critical temperature and the critical time period. According to some exemplary embodiments, the heat treatment temperature is determined as being about ninety-five percent of the critical temperature. According to some exemplary embodiments, the heat treatment time period is determined as being about ninety-five percent of the critical time period. In certain exemplary embodiments, the heat treatment temperature ranges from about eighty-five percent to about ninety-eight percent of the critical temperature, but remains above 750° C. In other exemplary embodiments, the heat treatment temperature ranges from about eighty-five percent to about ninety-eight percent of the critical temperature, but remains above 850° C. In certain exemplary embodiments, the heat treatment time period ranges from about thirty percent to about ninety-eight percent of the critical time period. In other exemplary embodiments, the heat treatment time period ranges from about thirty percent to about ninety-eight percent of the critical time period but is less than thirty minutes. For example, if the critical temperature is 850° C. and the critical time period is ten minutes, the heat treatment temperature can be 800° C., which is above the lower limit of 750° C., and the heat treatment time period can be five minutes. Hence, the heat treatment temperature and the heat treatment time period both fall within this acceptable range. Alternatively, in other exemplary embodiments, one of either the critical temperature or the critical time period becomes the heat treatment temperature or the heat treatment time period, respectively, while the other is reduced into any of the ranges described above. Thus, according to the above provided example, the heat treatment temperature can be 850° C., which is the same as the critical temperature, and the heat treatment time period can be five minutes, which is fifty percent of the critical time period. Alternatively, in yet other exemplary embodiments, one of either the critical temperature or the critical time period is reduced to the range provided above, while the other is reduced, maintained, or even increased when ascertaining the heat treatment temperature and the heat treatment time period as long as the combination has been tested and results provide for better structural integrity of the component, or less residual stresses present therein.

In other exemplary embodiments, the heat treatment temperature is determined as being about 50° C. less than the critical temperature. According to some exemplary embodiments, the heat treatment time period is determined as being about five minutes less than the critical time period. In certain exemplary embodiments, the heat treatment temperature ranges from about 10° C. to about 100° C. less than the critical temperature, but remains above 750° C. In other exemplary embodiments, the heat treatment temperature ranges from about 10° C. to about 100° C. less than the critical temperature, but remains above 850° C. In certain exemplary embodiments, the heat treatment time period ranges from about two minutes to about ten minutes less than the critical time period. In other exemplary embodiments, the heat treatment time period ranges from about two minutes to about ten minutes less than the critical time period, but is less than thirty minutes. For example, if the critical temperature is 850° C. and the critical time period is ten minutes, the heat treatment temperature can be 800° C., which is above the lower limit of 750° C., and the heat treatment time period can be five minutes. Hence, the heat treatment temperature and the heat treatment time period both fall within this acceptable range. Alternatively, in other exemplary embodiments, one of either the critical temperature or the critical time period becomes the heat treatment temperature or the heat treatment time period, respectively, while the other is reduced into any of the ranges described above. Thus, according to the above provided example, the heat treatment temperature can be 850° C., which is the same as the critical temperature, and the heat treatment time period can be five minutes, which is five minutes less than the critical time period. Alternatively, in yet other exemplary embodiments, one of either the critical temperature or the critical time period is reduced to the range provided above, while the other is reduced, maintained, or even increased when ascertaining the heat treatment temperature and the heat treatment time period as long as the combination has been tested and results provide for better structural integrity of the component, or less residual stresses present therein.

According to some exemplary embodiments, the heat treatment temperature ranges from about 750° C. to about 900° C. and the heat treatment time period ranges from about thirty seconds to less than thirty minutes. According to some other exemplary embodiments, the heat treatment temperature ranges from about 750° C. to about 900° C. and the heat treatment time period ranges from about thirty seconds to less than fifteen minutes. According to yet some other exemplary embodiments, the heat treatment temperature ranges from about 750° C. to about 900° C. and the heat treatment time period ranges from about thirty seconds to less than ten minutes. According to further exemplary embodiments, the heat treatment temperature ranges from about 800° C. to about 900° C. and the heat treatment time period ranges from about thirty seconds to less than fifteen minutes. According to further exemplary embodiments, the heat treatment temperature ranges from about 850° C. to about 900° C. and the heat treatment time period ranges from about thirty seconds to less than fifteen minutes. According to some further exemplary embodiments, the heat treatment temperature ranges from about 850° C. to about 900° C. and the heat treatment time period ranges from about thirty seconds to less than thirty minutes.

The residual stress reduction method 300 proceeds to step 350. At step 350, a high temperature heat treatment process is performed on the one or more remaining, components. During the high temperature heat treatment process, one or more remaining components from the component category are heated to about the heat treatment temperature for about the heat treatment time period. The high temperature heat treatment process is described in further detail below with respect to FIGS. 6-8B.

The residual stress reduction method 300 proceeds to step 360. At step 360, the residual stress reduction method 300 ends. According to certain exemplary embodiments, a portion of the catalyst material from the polycrystalline structure of the one or more components is removed (via a leaching process or an electro-chemical process) after performing a high temperature heat treatment process on the one or more remaining components. Alternatively, a portion of the catalyst material from the polycrystalline structure of the one or more components is removed (via a leaching process or an electro-chemical process) before performing a high temperature heat treatment process on the one or more remaining components.

Figure 4:
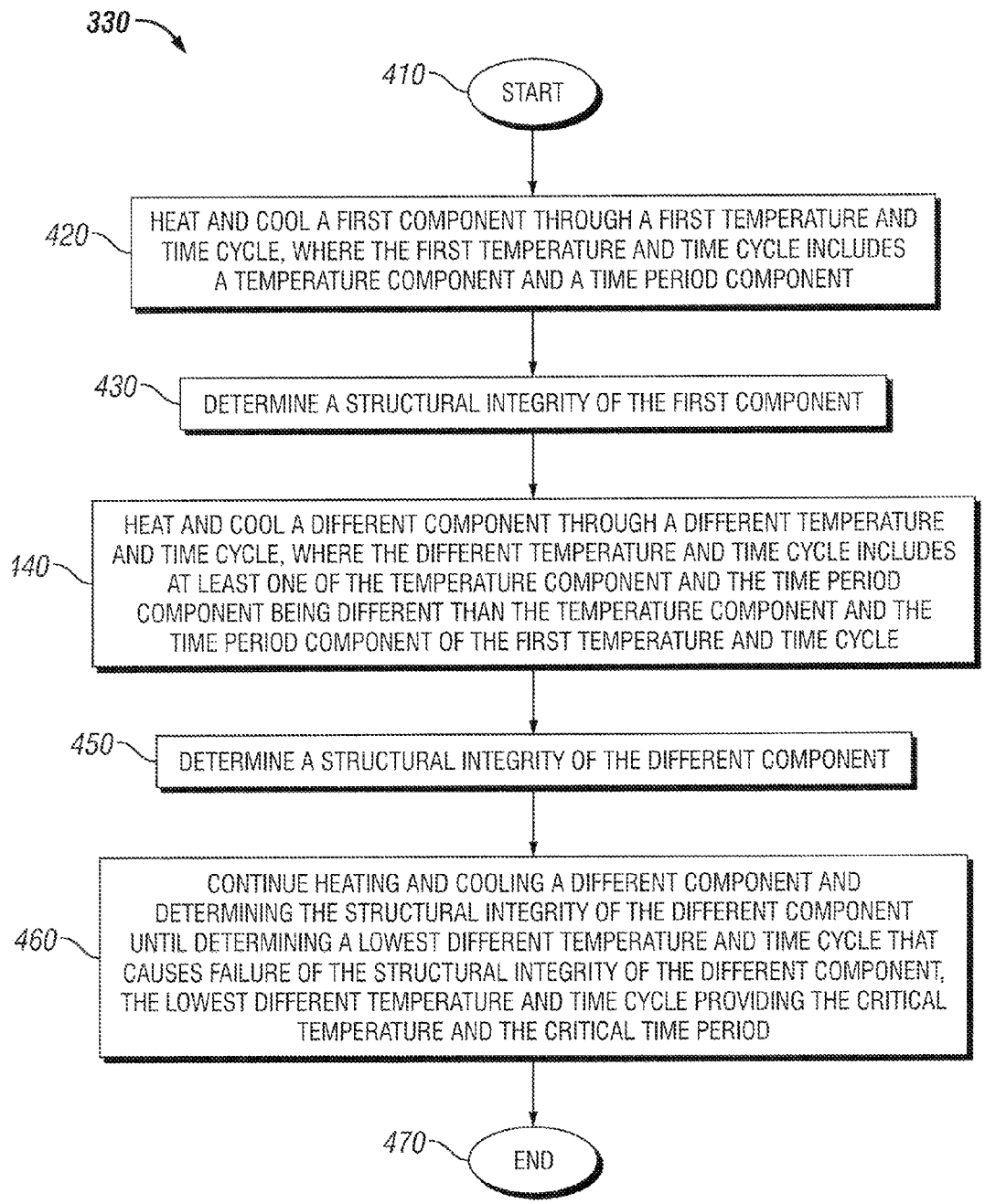
FIG. 4 is a flowchart depicting a critical temperature and time period determination method in accordance with an exemplary embodiment of the present invention.

FIG. 4 is a flowchart depicting the critical temperature and time period determination method 330, as mentioned in the residual stress reduction method 300 above, in accordance with an exemplary embodiment of the present invention. Although FIG. 4 shows a series of steps depicted in a certain order, the order of one or more steps can be rearranged, combined, into fewer steps, and/or separated into more steps than that shown in other exemplary embodiments. Referring to FIG. 4 the critical temperature and time period determination method 330 begins at step 410. Upon starting at step 410, the critical temperature and time period determination method 330 proceeds to step 420.

At step 420, a first component is heated and cooled through a first temperature and time cycle. The first temperature and time cycle includes a temperature component and a time period component. For example, if the first temperature and time cycle is 800° C. at five minutes, the temperature component is 800° C. and the time period component is five minutes. Thus, in this example, the first component is heated to 800° C., held at that temperature for five minutes, and then allowed to cool. The starting temperature of the first component is about room temperature in some exemplary embodiments, while in other exemplary embodiments, the starting temperature of the first component is about −150° C. to about −200° C., or ranges anywhere from ambient to −200° C. In some exemplary embodiments, the heating is performed gradually, while in other exemplary embodiments, the heating is performed rapidly, such that, for example, the first component is heated from room temperature to 800° C. within minutes, such as within two to ten minutes. In this example, the component can be dropped into a chamber or bath that is already at the desired temperature, thereby allowing the component to reach the desired temperature rapidly. Yet in some other alternative exemplary embodiments, the first component can be pre-heated to a desired temperature and then heated, either gradually and/or rapidly, to this 800° C. temperature. In certain exemplary embodiments, the pre-heated desired temperature ranges between 500° C. to 600° C., however this range is different in other exemplary embodiments. Further, in certain exemplary embodiments, the first component is allowed to cool to room temperature gradually in ambient air. Alternatively, the cooling is performed more rapidly, such as within minutes.

The critical temperature and time period determination method 330 proceeds to step 430. At step 430, the structural integrity of the first component is determined. The structural integrity of the component is comparable to the hardness of the component according to some exemplary embodiments. In certain exemplary embodiments, the structural integrity is determined using an acoustic emission testing device (not shown), which is described in detail in U.S. patent application Ser. No. 12/754,784, entitled "Acoustic Emission Toughness Testing For PDC, PCBN, Or Other Hard Or Superhard Material Inserts" and filed on Apr. 6, 2010, which has already been incorporated by reference in its entirety herein. The structural integrity of the first component is determined by other known methods, apparatuses, and systems in other exemplary embodiments. Steps 420 and 430, in some exemplary embodiments, are performed multiple times, such as ten times, through the same first temperature and time cycle to obtain a statistical meaningful sample. For example, an average, a twenty-five percentile, and a seventy-five percentile is obtained in certain exemplary embodiments.

The critical temperature and time period determination method 330 proceeds to step 440. At step 440, a different component is heated and cooled through a different temperature and time cycle. The different temperature and time cycle includes a temperature component and a time period component, where at least one of the temperature component and the time period component is different than the temperature component and the time period component of the first temperature and time cycle. For example, the different temperature and time cycle can be 850° C. at ten minutes, where both the temperature component and the time period component is different than the temperature component and the time period component of the first temperature and time cycle. In another example, the different temperature and time cycle can be 850° C. at five minutes, where only the temperature component is different than the temperature component of the first temperature and time cycle. Thus, according to one of the examples provided above, the different component is heated to 850° C., held at that temperature for ten minutes, and then allowed to cool. The starting temperature of the different component is about room temperature in some exemplary embodiments, while in other exemplary embodiments, the starting temperature of the different component is about −150° C. to about −200° C., or ranges anywhere from about ambient to about −200° C. In some exemplary embodiments, the heating is performed gradually, while in other exemplary embodiments, the heating is performed rapidly, such that, for example, the different component is heated from room temperature to 850° C. within minutes, such as within five to ten minutes. Yet in some other alternative exemplary embodiments, the different component can be pre-heated to a desired temperature and then heated, either gradually and/or rapidly, to this 850° C. temperature. In certain exemplary embodiments, the pre-heated desired temperature ranges between 500° C. to 600° C., however this range is different in other exemplary embodiments. Further, in certain exemplary embodiments, the different component is allowed to cool to room temperature gradually in ambient air. Alternatively, the cooling is performed more rapidly, such as within minutes.

The critical temperature and time period determination method 330 proceeds to step 450. At step 450, the structural integrity of the different component is determined. As previously mentioned, the structural integrity of the component is comparable to the hardness of the component according to some exemplary embodiments. In certain exemplary embodiments, the structural integrity is determined using the acoustic emission testing device (not shown), which is described in detail in U.S. patent application Ser. No. 12/754,784, entitled "Acoustic Emission Toughness Testing For PDC, PCBN, Or Other Hard Or Superhard Material Inserts" and filed on Apr. 6, 2010, which has already been incorporated by reference in its entirety herein. The structural integrity of the different component is determined by other known methods, apparatuses, and systems in other exemplary embodiments. Steps 440 and 450, in some exemplary embodiments, are performed multiple times on the different component, such as ten times, through the same different temperature and time cycle to obtain a statistical meaningful sample. For example, an average, a twenty-five percentile, and a seventy-five percentile is obtained in certain exemplary embodiments.

The critical temperature and time period determination method 330 proceeds to step 460. At step 460, heating and cooling a different component and determining the structural integrity of the different component is continued until a lowest different temperature and time cycle that causes failure of the structural integrity of the component is determined. The lowest different temperature and time cycle provides the critical temperature and the critical time period.

The critical temperature and time period determination method 330 proceeds to step 470. At step 470, the critical temperature and time period determination method 330 ends.

Figure 5:
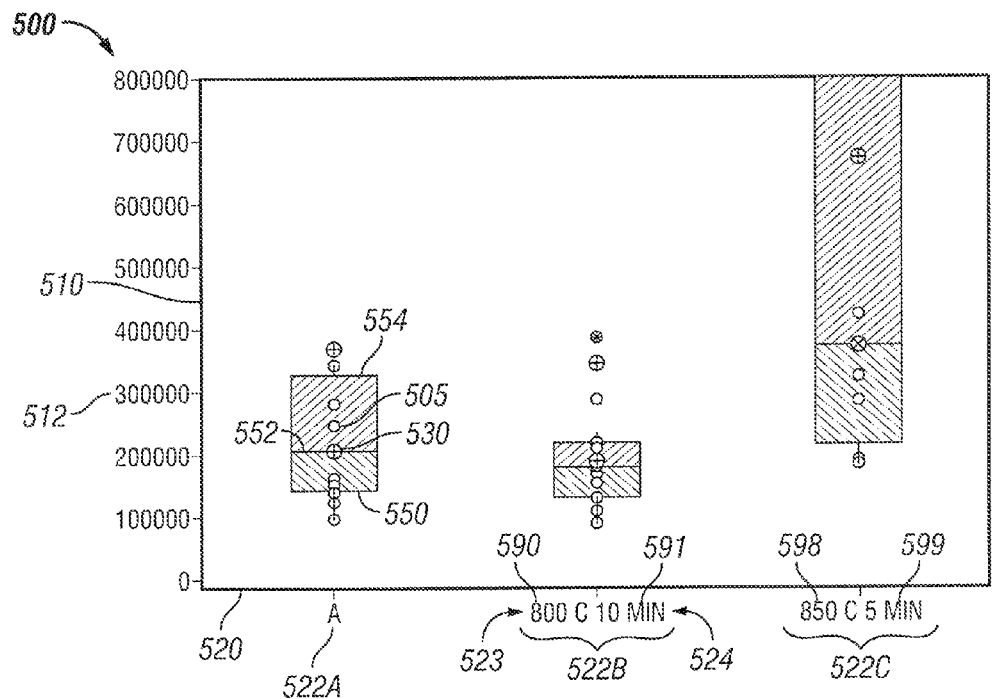
FIG. 5 is a graphical chart depicting structural integrity of several components subjected to various temperature and time cycles in accordance with an exemplary embodiment of the present invention.

FIG. 5 is a graphical chart 500 depicting structural integrity of several components 505 subjected to various temperature and time cycles 522 in accordance with an exemplary embodiment of the present invention. FIG. 5 graphically represents at least a portion of the critical temperature and time period determination method 330 (FIG. 4). Referring to FIG. 5, the graphical chart 500 includes a temperature and time cycle axis 520 and a structural integrity axis 510. The temperature and time cycle axis 520 includes one or more temperature and time cycles 522, where each temperature and time cycle 522 includes a temperature component 523 and a time period component 524. The structural integrity axis 510 includes structural integrity values 512 measured for the one or more components 505. A structural integrity data point 530 is obtained by measuring the structural integrity value 512, or hardness, of the component 505 using the acoustic emission testing device mentioned above. However, as previously mentioned, other devices and methods known to people having ordinary skill in the art can be used to determine the structural integrity of the component. Each structural integrity data point 530 is plotted on the graphical chart 500. Several components 505 from the same component category has its structural integrity value 512 measured after being treated under a certain temperature and time cycle 522. In some exemplary embodiments, the structural integrity 512 for ten components 505 are obtained for each temperature and time cycle 522, however, the number of components measured for each temperature and time cycle 522 is greater or fewer in other exemplary embodiments. In some exemplary embodiments, a twenty-five percentile marking 550, a fifty percentile marking 552 (or average), and a seventy-five percentile marking 554 is shown in the chart 500 for each temperature and time cycle 522. The area between the twenty-five percentile marking 550 and the seventy-five percentile marking 554 is shaded. The amount of data scattering is ascertained using this graphical chart 500 and can be one or more of a differential between the highest and lowest structural integrity values 512 for each temperature and time cycle 522, a range between the twenty-five percentile marking 550 and the seventy-five percentile marking 554, or some similar observation made from the graphical chart 500. Accordingly, the less data scattering present represents better structural integrity of the component and hence less residual stresses therein. Additionally, or in lieu of the amount of data scattering, the structural integrity can be determined using the mean or median structural integrity value.

According to FIG. 5 only, structural integrity values 512 are measured on components 505 exposed to three different temperature and time cycles 522. The first temperature and time cycle 522A is referenced as "A" and has not been heat treated. Thus, the temperature component 523 is ambient temperature and the time period component 524 is zero minutes. The structural integrity values 512 for components exposed to the first temperature and time cycle 522A exhibit some scattering. The second temperature and time cycle 522B is referenced as "800 C 10 min". Thus, the temperature component 523 is 800° C. and the time period component 524 is ten minutes. The structural integrity values 512 for components exposed to the second temperature and time cycle 522B exhibit less scattering than components exposed to the first temperature and time cycle 522A. Hence, the components exposed to the second temperature and time cycle 522B are more stable and harder than the components exposed to the first temperature and time cycle 522A. The third temperature and time cycle 522C is referenced as "850 C 5 min". Thus, the temperature component 523 is 850° C. and the time period component 524 is five minutes. The structural integrity values 512 for components exposed to the third temperature and time cycle 522C exhibit more scattering than components exposed to either of the first temperature and time cycle 522A and the second temperature and time cycle 522B. Hence, the components exposed to the third temperature and time cycle 522C is less stable and less hard, or is structurally impaired, than the components exposed to either the first temperature and time cycle 522A or the second temperature and time cycle 522B. Pursuant to FIG. 5, the critical temperature 598 is 850° C. and the critical time period 599 is five minutes, which is the temperature component 523 and the time period component 524 of the temperature and time cycle 522 when the component becomes structurally impaired. Hence, the heat treatment temperature 590 and the heat treatment time period 591 can be 800° C. and ten minutes, respectively, according to FIG. 5 and pursuant to the description provided above.

Figure 6:
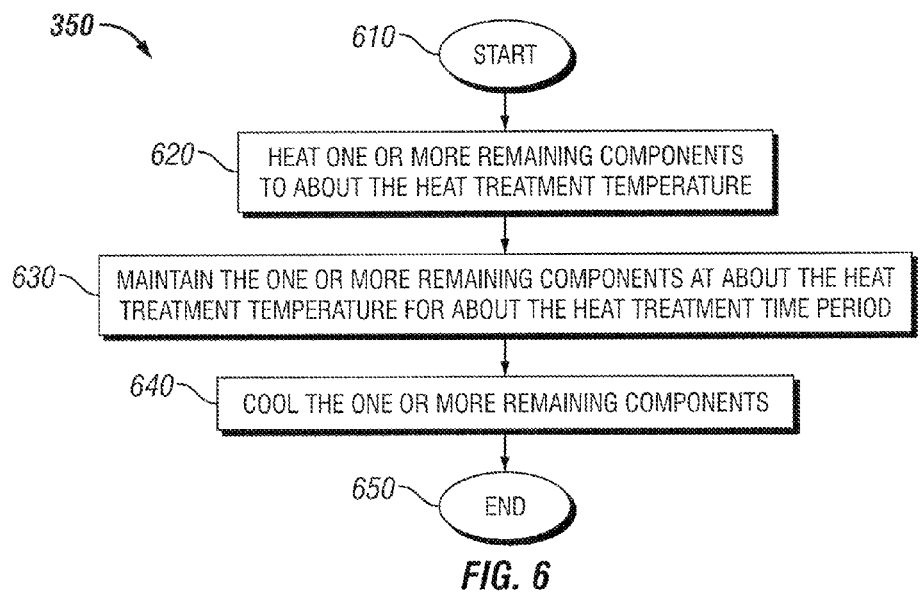
FIG. 6 is a flowchart depicting a high temperature heat treatment process in accordance with an exemplary embodiment of the present invention.

FIG. 6 is a flowchart depicting a high temperature heat treatment process 350 in accordance with an exemplary embodiment of the present invention. Although FIG. 6 shows a series of steps' depicted in a certain order, the order of one or more steps can be rearranged, combined into fewer steps, and/or separated into more steps than that shown in other exemplary embodiments. Referring to FIG. 6 the high temperature heat treatment process 350 begins at step 610. Upon starting at step 610, the high temperature heat treatment process 350 proceeds to step 620.

At step 620, one or more remaining components are heated to about the heat treatment temperature. The remaining components are similar to the components described above and are from the same or similar component category. Thus, the heat treatment temperature determined for the component also is applicable to the remaining components and the structural integrity of the remaining components will not be impaired when brought to the heat treatment temperature for the heat treatment time period. The remaining components typically start at ambient temperature and is heated, either gradually and/or rapidly, to the heat treatment temperature. The determination of the heat treatment temperature is described above in detail and is not repeated again for the sake of brevity. Alternatively, the remaining components are heated, either gradually and/or rapidly, to an intermediate temperature and then heated again, either gradually and/or rapidly, to the heat treatment temperature. The intermediate temperature is a temperature selected between the starting temperature and the heat treatment temperature. The temperature of the remaining components can be held for a period of time at the intermediate temperature. In yet other exemplary embodiments, the starting temperature of the remaining components can be below ambient temperature, such as between −100° C. and −200° C.

The high temperature heat treatment process 350 proceeds to step 630. At step 630, the one or more remaining components are maintained at about the heat treatment temperature for about the heat treatment time period. The determination of the heat treatment time period is described in detailed above and is not repeated herein for the sake of brevity.

The high temperature heat treatment process 350 proceeds to step 640. At step 640, the one or more remaining components are cooled. In certain exemplary embodiments, the one or more components are cooled gradually in air. In other exemplary embodiments, the one or more remaining components are cooled, either gradually and/or rapidly, back to ambient temperature.

The high temperature heat treatment process 350 proceeds to step 650. At step 650, the high temperature heat treatment process 350 ends.

Figure 7:
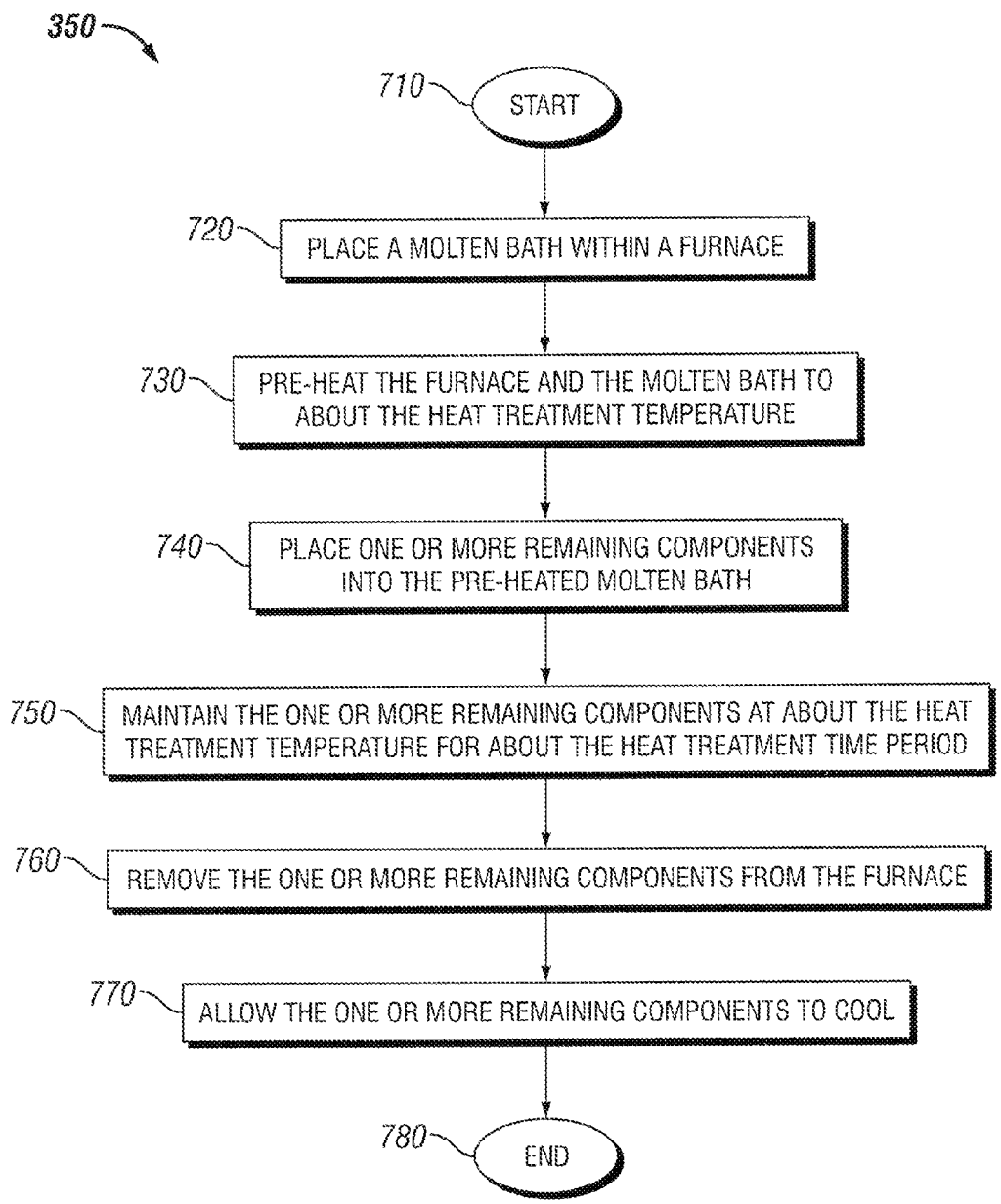
FIG. 7 is a flowchart depicting a high temperature heat treatment process in accordance with another exemplary embodiment of the present invention.

FIG. 7 is a flowchart depicting a high temperature heat treatment process 350 in accordance with another exemplary embodiment of the present invention. Although FIG. 7 shows a series of steps depicted in a certain order, the order of one or more steps can be rearranged, combined into fewer steps, and/or separated into more steps than that shown in other exemplary embodiments. Referring to FIG. 7 the high temperature heat treatment process 350 begins at step 710. Upon starting at step 710, the high temperature heat treatment process 350 proceeds to step 720.

At step 720, a molten bath is positioned within a furnace. The molten bath and the furnace are both illustrated in FIGS. 8A and 8B and is discussed in further detail below. Briefly mentioning, the molten bath includes a tray with a molten material placed therein. According to some exemplary embodiments, the molten bath is a flux bath having a flux material placed therein. The molten material is used to control the atmosphere within the furnace and prevent oxygen from contacting the components once the components are placed into the molten bath. Some examples of the molten material include, but are not limited to, molten copper, molten tin, sodium chloride, borosilicate, or other materials that are capable of a high heat transfer.

The high temperature heat treatment process 350 proceeds to step 730. At step 730, the furnace and the molten bath are pre-heated to about the heat treatment temperature. The determination of the heat treatment temperature has been previously described in detailed and is not repeated herein for the sake of brevity.

The high temperature heat treatment process 350 proceeds to step 740. At step 740, one or more remaining components are placed into the pre-heated molten bath. The components are entirely submerged within the molten material so that they are not exposed to oxygen during this part of the process.

The high temperature heat treatment process 350 proceeds to step 750. At step 750, the one or more remaining components are maintained at about the heat treatment temperature for about the heat treatment time period. The determination of the heat treatment time period is described in detailed above and is not repeated herein for the sake of brevity. According to some exemplary embodiments, the heat treatment period is about five to seven minutes, but this heat treatment period is different in other exemplary embodiments.

The high temperature heat treatment process 350 proceeds to step 760. At step 760, the one or more remaining components are removed from the furnace. According to some exemplary embodiments, the one or more remaining components are removed from the molten bath in addition to being removed from the furnace. For example, tongs, or other suitable devices, are used to remove the remaining cutters from the furnace and the molten bath. However, in other exemplary embodiments, the one or more remaining components are removed from the furnace by removing the entire molten bath from the furnace.

The high temperature heat treatment process 350 proceeds to step 770. At step 770, the one or more remaining components are cooled. In certain exemplary embodiments, the one or more components are cooled gradually in air. In other exemplary embodiments, the one or more remaining components are cooled, either gradually and/or rapidly, back to ambient temperature.

The high temperature heat treatment process 350 proceeds to step 780. At step 780, the high temperature heat treatment process 350 ends.

According to some alternative exemplary embodiments, the furnace uses different methods and/or apparatuses to achieve an oxygen-free environment for the components to be placed therein in lieu of, or in addition to the molten bath. For example, the furnace can operate in vacuum conditions, in argon atmosphere, in nitrogen atmosphere, or other inert gas atmospheres. Further, in lieu of the furnace, an induction unit is used in the above mentioned process where a gas is introduced into a chamber of the induction unit. The gas is argon, for example, but is other gases in other exemplary embodiments. These induction units are known to persons having ordinary skill in the art and are not described herein in detail for the sake of brevity.

Figure 8A:
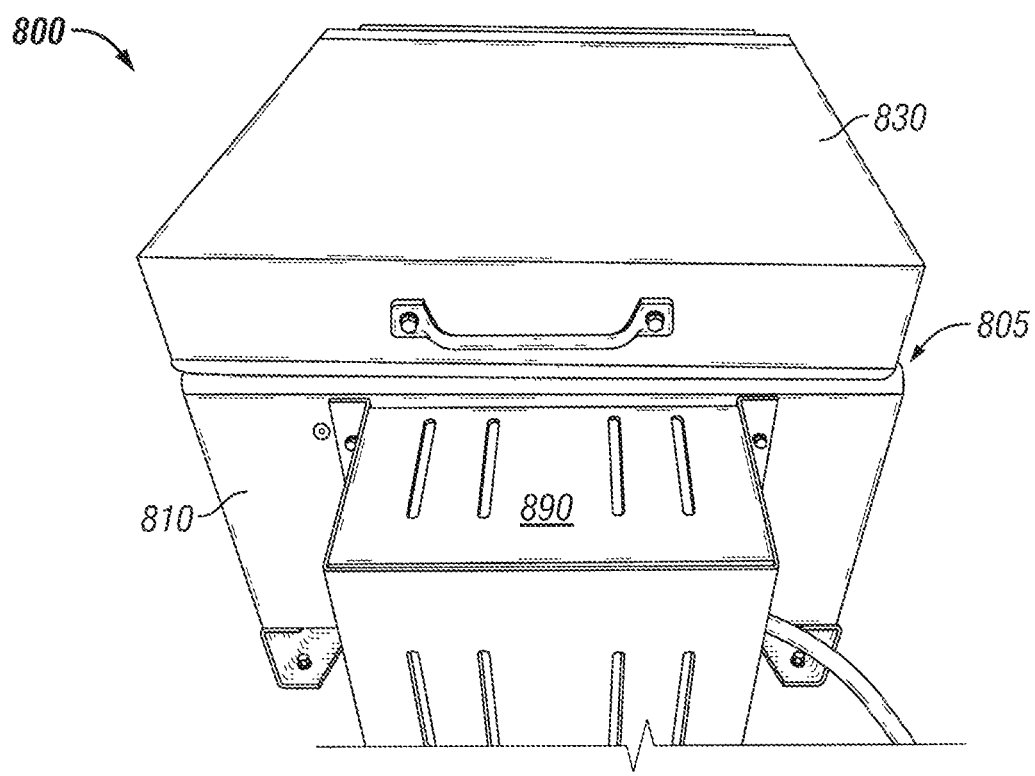
FIG. 8A is a perspective view of a furnace in a closed orientation in accordance with an exemplary embodiment of the present invention.
Figure 8B:
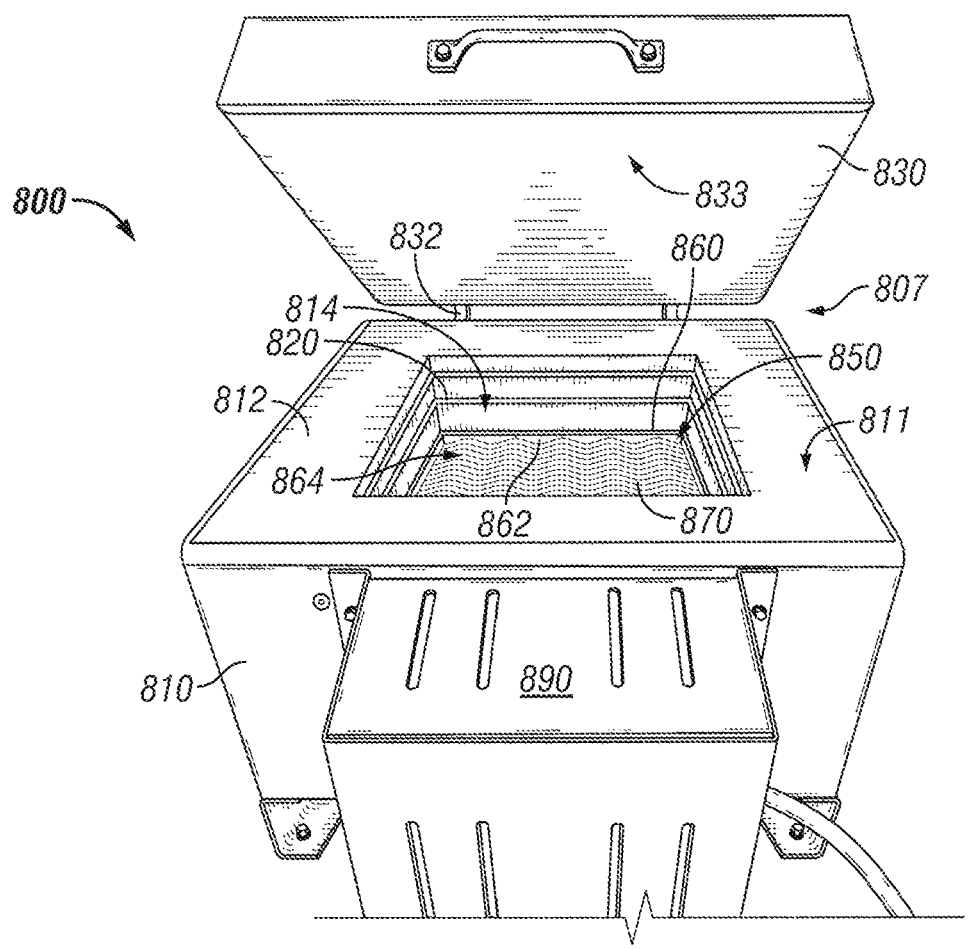
FIG. 8B is a perspective view of the furnace of FIG. 8A in an open orientation with a molten bath positioned therein in accordance with an exemplary embodiment of the present invention.

FIG. 8A is a perspective view of a furnace 800 in a closed orientation 805 in accordance with an exemplary embodiment of the present invention. FIG. 8B is a perspective view of the furnace 800 in an open orientation 807 with a molten bath 850 positioned therein in accordance with an exemplary embodiment of the present invention. Referring to FIGS. 8A and 8B, the furnace 800 includes a base 810, one or more heating elements 820, and a cover 830. Also referring to FIGS. 8A and 8B, the molten bath 850 includes a tray 860 and molten material 870.

The base 810 includes one or more walls 812 that define a cavity 814 therein. According to some exemplary embodiments, the base 810 includes four walls 812 that are shaped into a rectangular configuration; however, other shapes can be formed in alternative exemplary embodiments. The base 810 is fabricated using materials that can withstand high temperatures, such as the 850° C. to 900° C. that may be seen according to the present disclosure.

One or more heating elements 820 are coupled to the walls 812 within the cavity 814 and are oriented to direct heat into the cavity 814. These heating elements 820 are able to raise the temperature within the cavity 814 to at least the critical temperature. According to some exemplary embodiments, the heating elements 820 are powered using an external power source 890, which may be coupled to the base 810; however, the power source is located elsewhere in other exemplary embodiments.

The cover 830 is removably positioned over the cavity 814. According to some exemplary embodiments, the cover 830 is coupled to the base 810 using one or more hinges 832. The cover 830 is typically fabricated using the same or similar material as that used in fabricating the walls 812. FIG. 8A shows the cover 830 in the closed orientation 805 whereby a bottom surface 833 of the cover 830 is placed over the cavity 814 and adjacent to a top surface 811 of the base 810. Conversely, FIG. 8B shows the cover 830 in the open orientation 807 whereby the cavity 814 is now visible.

The molten bath 850 is inserted into the cavity 814 of the furnace 800. As previously mentioned, the molten bath 850 includes the tray 860 and the molten material 870. The tray 860 is dimensioned to fit within the cavity 814 of the furnace 800. The tray 860 also includes one or more tray walls 862 that define a tray cavity 864 therein. The tray 860 is fabricated using suitable materials that are not damaged when exposed to temperatures during the process described above.

The molten material 870 is inserted into the tray cavity 864 and is filled to a depth such that the molten material 870 completely surrounds the components when placed in the tray cavity 864. One example of the molten material 870 is borosilicate; however, other suitable materials can be used, such as certain phosphates, tin, copper, and sodium chloride, without departing from the scope and spirit of the exemplary embodiments.

Figure 9A:
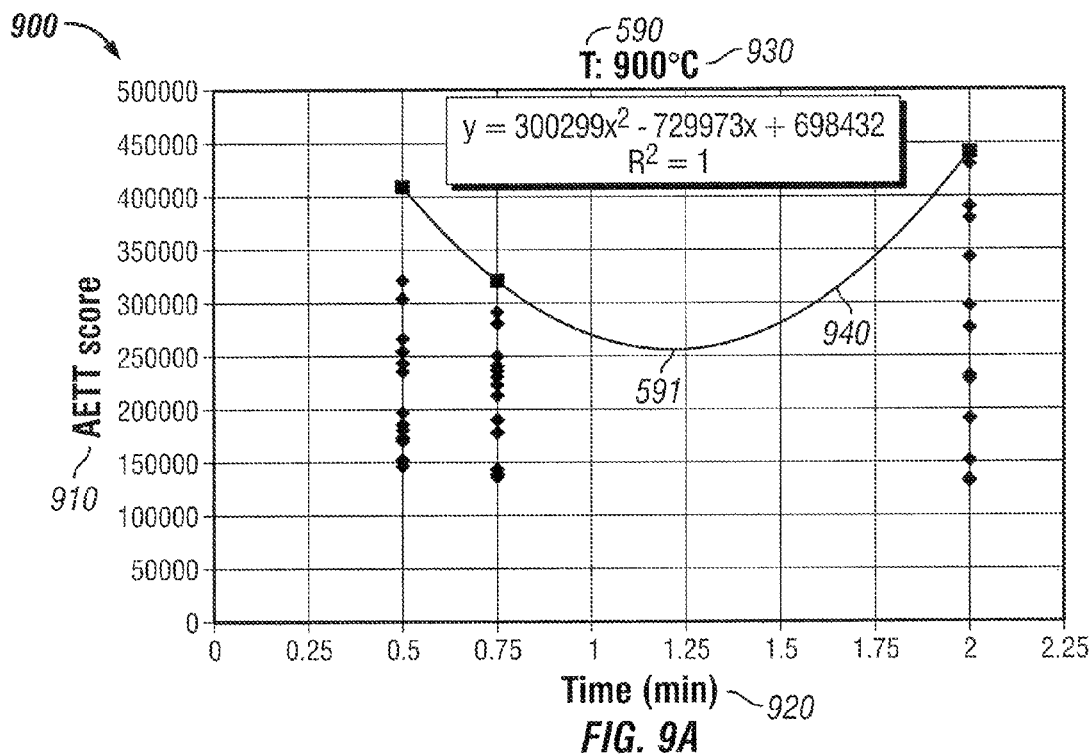
FIG. 9A is a graphical representation showing the relationship between AETT scores and treatment time when treatment temperature is held constant according to an exemplary embodiment of the present invention.

FIG. 9A is a graphical representation 900 showing the relationship between AETT scores 910 and treatment time 920 when treatment temperature 930 is held constant according to an exemplary embodiment of the present invention. Referring to FIG. 9A, the graphical representation 900 includes an acoustic emission toughness testing (AETT) score axis 910, a treatment time axis 920, and a time limiting curve 940. The AETT score axis 910 is represented by a y-axis. The treatment time axis 920 is represented by an x-axis and is provided with units in the minutes. The time limiting curve 940 is illustrated on the graphical representation 900. In determining the time limiting curve 940, the treatment temperature 930 is held constant while several cutters, or components having a polycrystalline structure, are subjected to various treatment times 920. The heat treated cutters are then tested under an AETT testing procedure to obtain a corresponding AETT score 910 for each heat treated cutter. The AETT testing procedure is described in U.S. patent application Ser. No. 12/754,784, entitled "Acoustic Emission Toughness Testing For PDC, PCBN, Or Other Hard Or Superhard Material Inserts" and filed on Apr. 6, 2010, which has been incorporated by reference herein. Each AETT score 910 and corresponding treatment time 920 for each cutter is plotted on the graphical representation 900. The time limiting curve 940 is then determined by fitting a parabolic interpolation through each of the highest AETT scores 910 for every tested treatment time 920.

According to FIG. 9A, a number of cutters of the same type and brand were tested at various treatment times 920 and at a constant treatment temperature 930. The treatment temperature 930 was held constant at 900° C. Fourteen cutters were heat treated at 0.5 minutes. Fourteen cutters were heat treated at 0.75 minutes. Twelve cutters were heat treated at two minutes. Although a specific number of cutters were heat treated at different times, any number of cutters can be tested so that a statistical meaningful sample is obtained. The heat treated cutters were then tested to determine their respective AETT scores 910. Each AETT score 910 and corresponding treatment time 920 for each cutter was plotted on the graphical representation 900. The time limiting curve 940 was then determined by fitting a parabolic interpolation through each of the highest AETT scores 910 for every tested treatment time 920. According to some exemplary embodiments, the time limiting curve 940 was determined to be $y=300299x^2-729973x+698432$. According to the time limiting curve 940, the cutters treated for 0.5 minutes had a larger AETT score than the cutters treated for 0.75 minutes. Thus, the cutters treated for 0.75 minutes were structurally better than the cutters treated for 0.5 minutes. Additionally, the cutters treated for two minutes had a larger AETT score than the cutters treated for 0.75 minutes or the cutters treated for 0.5 minutes. Thus, the cutters treated for two minutes were structurally worse than either the cutters treated for 0.5 minutes or the cutters treated for 0.75 minutes. The heat treatment time period 591 is found at the lowest point on the time limiting curve 940. Hence, at 900°

C., the heat treatment temperature 590 is 900° C. and the heat treatment time period 591 is about 1.22 minutes, as determined from the graphical representation 900.

Figure 9B:
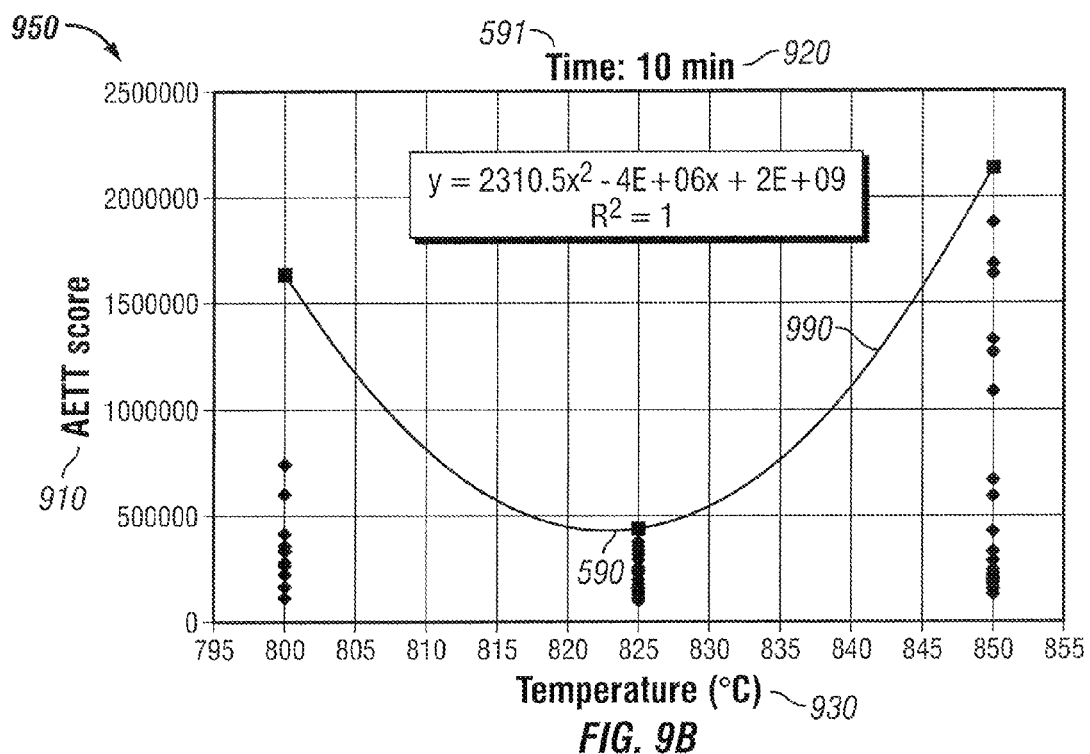
FIG. 9B is a graphical representation showing the relationship between AETT scores and treatment temperature when treatment time is held constant according to an exemplary embodiment of the present invention.

FIG. 9B is a graphical representation 950 showing the relationship between AETT scores 910 and treatment temperature 930 when treatment time 920 is held constant according to an exemplary embodiment of the present invention. Referring to FIG. 9B, the graphical representation 950 includes an acoustic emission toughness testing (AETT) score axis 910, a treatment temperature axis 920, and a temperature limiting curve 990. The AETT score axis 910 is represented by a y-axis. The treatment temperature axis 930 is represented by an x-axis and is provided with units in the degrees Celcius. The temperature limiting curve 990 is illustrated on the graphical representation 950. In determining the temperature limiting curve 990, the treatment time 920 is held constant while several cutters, or components having a polycrystalline structure, are subjected to various treatment temperatures 930. The heat treated cutters are then tested under an AETT testing procedure to obtain a corresponding AETT score 910 for each heat treated cutter. The AETT testing procedure is described in U.S. patent application Ser. No. 12/754,784, entitled "Acoustic Emission Toughness Testing For PDC, PCBN, Or Other Hard Or Superhard Material Inserts" and filed on Apr. 6, 2010, which has been incorporated by reference herein. Each AETT score 910 and corresponding treatment temperature 930 for each cutter is plotted on the graphical representation 950. The temperature limiting curve 990 is then determined by fitting a parabolic interpolation through each of the highest AETT scores 910 for every tested treatment temperature 930.

According to FIG. 9B, a number of cutters of the same type and brand were tested at various treatment temperatures 930 and at a constant treatment time 920. The treatment time 920 was held constant at ten minutes. Eleven cutters were heat treated at 800° C. Fourteen cutters were heat treated at 825° C. Nineteen cutters were heat treated at 850° C. Although a specific number of cutters were heat treated at different temperatures, any number of cutters can be tested so that a statistical meaningful sample is obtained. The heat treated cutters were then tested to determine their respective AETT scores 910. Each AETT score 910 and corresponding treatment temperature 930 for each cutter was plotted on the graphical representation 950. The temperature limiting curve 990 was then determined by fitting a parabolic interpolation through each of the highest AETT scores 910 for every tested treatment temperature 930. According to some exemplary embodiments, the temperature limiting curve 990 was determined to be $y=2310.5x^2-(4E+6)x+(2E+9)$. According to the temperature limiting curve 990, the cutters treated at 800° C. had a larger AETT score than the cutters treated at 825° C. Thus, the cutters treated at 825° C. were structurally better than the cutters treated at 800° C. Additionally, the cutters treated at 850° C. had a larger AETT score than the cutters treated at 800° C. or the cutters treated at 825° C. Thus, the cutters treated for 850° C. were structurally worse than either the cutters treated at 800° C. or the cutters treated at 825° C. The heat treatment temperature 590 is found at the lowest point on the temperature limiting curve 990. Hence, at ten minutes, the heat treatment time period 591 is ten minutes and the heat treatment temperature 590 is about 823° C., as determined from the graphical representation 950.

Some embodiments of the invention disclosed herein represent substantial improvements in terms of polycrystalline compact diamond (PCD) cutters stress relieving high temperature cycles. Depending on the composition and particle size distribution (grain size) of different PCDs, unique combinations of heat treatment time periods and heat treatment temperatures are defined to perform the most beneficial stress relieving cycle.

Although each exemplary embodiment has been described in detail, it is to be construed that any features and modifications that are applicable to one embodiment are also applicable to the other embodiments. Furthermore, although the invention has been described with reference to specific embodiments, these descriptions are not meant to be construed in a limiting sense. Various modifications of the disclosed embodiments, as well as alternative embodiments of the invention will become apparent to persons of ordinary skill in the art upon reference to the description of the exemplary embodiments. It should be appreciated by those of ordinary skill in the art that the conception and the specific embodiments disclosed may be readily utilized as a basis for modifying or designing other structures or methods for carrying out the same purposes of the invention. It should also be realized by those of ordinary skill in the art that such equivalent constructions do not depart from the spirit and scope of the invention as set forth in the appended claims. It is therefore, contemplated that the claims will cover any such modifications or embodiments that fall within the scope of the invention.

The invention claimed is:

1. A post manufacture method for improving structural integrity of a cutter, comprising:
   obtaining a batch of cutters of a component category, each cutter having a polycrystalline diamond cutting table with catalyst material deposited within interstitial spaces thereof;
   removing a portion of the catalyst material from each cutting table;
   after removal of the catalyst material, heating the batch in an induction unit for a period of time less than thirty minutes; and
   testing a structural integrity of a first sample of cutters from the batch using an acoustic emission toughness test.

2. The method of claim 1, further comprising maintaining an inert gas atmosphere in the induction unit during heating.

3. The method of claim 1, wherein the portion of the catalyst material is removed by leaching.

4. The method of claim 1, wherein the portion of the catalyst material is removed by an electrochemical process.

5. The method of claim 1, wherein:
   the first sample is tested before heating, and
   the method further comprises:
      testing the structural integrity of a second sample of cutters from the batch after heating.

6. The method of claim 1, wherein:
   each cutter further has a tungsten carbide substrate, and
   the catalyst material also binds the cutting table to the substrate.

7. The method of claim 1, wherein the catalyst material is selected from a group consisting of: cobalt, nickel, and Group VIII metals.

* * * * *